United States Patent
Guendel et al.

(10) Patent No.: US 10,796,481 B2
(45) Date of Patent: Oct. 6, 2020

(54) VISUALIZATION OF LUNG FISSURES IN MEDICAL IMAGING

(71) Applicant: Siemens Healthcare GmbH, Erlangen (DE)

(72) Inventors: Lutz Guendel, Erlangen (DE); Atilla Kiraly, San Jose, CA (US); Bernhard Geiger, Cranbury, NJ (US); Carol L. Novak, Newtown, PA (US)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 15/958,255

(22) Filed: Apr. 20, 2018

(65) Prior Publication Data

US 2019/0325645 A1    Oct. 24, 2019

(51) Int. Cl.
| | |
|---|---|
| *G06T 17/20* | (2006.01) |
| *A61B 5/08* | (2006.01) |
| *A61B 34/10* | (2016.01) |
| *G06T 7/187* | (2017.01) |
| *A61B 6/03* | (2006.01) |
| *A61B 6/00* | (2006.01) |
| *G06T 7/00* | (2017.01) |
| *G06T 11/00* | (2006.01) |
| *G06T 11/60* | (2006.01) |

(52) U.S. Cl.
CPC ............... *G06T 17/20* (2013.01); *A61B 5/08* (2013.01); *A61B 6/032* (2013.01); *A61B 6/5223* (2013.01); *A61B 34/10* (2016.02); *G06T 7/0012* (2013.01); *G06T 7/187* (2017.01); *G06T 11/001* (2013.01); *G06T 11/60* (2013.01); *A61B 2034/105* (2016.02); *G06T 2207/10081* (2013.01); *G06T 2207/30061* (2013.01)

(58) Field of Classification Search
CPC . G06T 2207/30061; G06T 2207/30064; G06T 17/20; G06T 19/20; G61B 5/08
See application file for complete search history.

(56) References Cited

U.S. PATENT DOCUMENTS

| | | | | |
|---|---|---|---|---|
| 5,883,933 | A * | 3/1999 | Goto | G06T 15/00 378/4 |
| 2007/0092864 | A1* | 4/2007 | Reinhardt | G06T 7/0012 435/4 |
| 2011/0052018 | A1* | 3/2011 | Blaffert | G06T 5/003 382/128 |

(Continued)

FOREIGN PATENT DOCUMENTS

WO    2014042902 A1    3/2014

OTHER PUBLICATIONS

Kiraly, Atilla P., et al. "Three-dimensional human airway segmentation methods for clinical virtual bronchoscopy." Academic radiology 9.10 (2002): 1153-1168.

(Continued)

*Primary Examiner* — Ryan McCulley

(57) ABSTRACT

Systems and methods are provided for generating a visualization of a lung fissure. Medical imaging data is processed to identify a lung mesh and fissures data. The lung mesh is augmented with the fissures data and projected onto a straight plane for rendering into a concise two-dimensional image in which completeness of the lung fissure may be detected.

16 Claims, 8 Drawing Sheets

(56) References Cited

U.S. PATENT DOCUMENTS

| | | | |
|---|---|---|---|
| 2012/0163687 A1* | 6/2012 | Plakas | G06T 7/74 382/131 |
| 2014/0079306 A1* | 3/2014 | Inoue | G06T 7/12 382/131 |
| 2014/0105472 A1* | 4/2014 | Yin | G06T 7/0012 382/128 |
| 2014/0275952 A1* | 9/2014 | Monroe | G06T 19/00 600/407 |
| 2015/0238270 A1* | 8/2015 | Raffy | A61B 34/10 600/407 |
| 2015/0254843 A1* | 9/2015 | Brown | G06T 7/0012 382/131 |
| 2016/0189373 A1* | 6/2016 | Park | A61B 6/032 382/131 |
| 2016/0328850 A1* | 11/2016 | Yin | A61B 5/055 |
| 2017/0224301 A1* | 8/2017 | Radhakrishnan | A61B 6/5217 |
| 2018/0047168 A1* | 2/2018 | Chen | G06T 7/11 |
| 2018/0085079 A1* | 3/2018 | Krimsky | G16H 50/50 |
| 2018/0085169 A1* | 3/2018 | Krimsky | A61B 34/10 |
| 2018/0235713 A1* | 8/2018 | Krimsky | A61B 34/20 |

OTHER PUBLICATIONS

Extended European Search Report (EESR) dated Sep. 30, 2019 in corresponding European Patent Application No.

Wei, et al. "Automatic recognition of major fissures in human lungs." International journal of computer assisted radiology and surgery 7.1 (2012): 111-123.

Shouliang, et al. "Automatic pulmonary fissure detection and lobe segmentation in CT chest images." Biomedical engineering online 13.1 (2014): 59.

\* cited by examiner

VISUALIZATION OF LUNG FISSURES IN MEDICAL IMAGING

BACKGROUND

The present embodiments relate to processing medical diagnostic images.

For the diagnosis and therapy of different lung diseases, lung fissures and lobes may be examined. The left lung is divided into two lobes, upper and lower. The division between these lobes forms the oblique (major) fissure. In the right lung, there is an oblique fissure and a horizontal fissure, separating the lung into three lobes—upper, middle, and lower.

In most people, the fissures separate the lobes and prevent gas and blood exchange. In some lung diseases, the separation is eroded. Additionally, fissure completeness is not guaranteed in even healthy individuals. In cases of incomplete fissures, therapies such as surgical or minimally invasive placement of endo-bronchial valves (EBV) are more likely to fail. Moreover, in the surgical resection of lung lobes, alternative methods have to be applied in case of incomplete fissures.

During an examination, the completeness of the fissures may be determined prior to selecting a treatment method. Locating incomplete fissure regions may also be potentially useful for therapy. A surgeon or technician may identify specifically the areas of the lung tissue that do not have indirect ventilation and are therefore candidates for valve therapy.

For examination of the lungs, thin slices from a computed tomography system may be used. The slices are two-dimensional and as such may not convey an entirety of a fissure that exists in three-dimensional space or the fissures may be difficult to identify. A three-dimensional model may be generated from multiple slices but requires additional resources, and a fissure may be occluded by other tissues or material.

BRIEF SUMMARY

By way of introduction, the preferred embodiments described below include methods and systems for generating a visualization of a lung fissure. Medical imaging data is processed to identify a lung mesh and fissure data. The lung mesh is augmented with the fissure data and projected onto a straight plane for rendering into a concise two-dimensional image in which completeness of the lung fissures may be detected.

In a first aspect, a method is provided for generating a visualization of a lung fissure. A medical image scanner acquires medical imaging data representing at least two adjacent lobes of a lung. An image processor generates a mesh of a boundary between at least two adjacent lobes from the medical imaging data, the mesh comprising a plurality of mesh voxels. The image processor identifies in the medical imaging data, fissure image data representing the lung fissure between the two adjacent lung lobes. The image processor augments the mesh with the identified fissure image data. The image processor generates a two-dimensional image of the augmented mesh projected onto a plane. The two-dimensional image is displayed.

In a second aspect, a method is provided for generating a visualization of a lung fissure. An image scanner acquires image data of a lung region. The image processor identifies lung data in the image data. The image processor identifies fissure data in the lung data. The image processor defines a point of view and generates from the point of view, a two-dimensional image of the fissure data and the lung data.

In a third aspect, an imaging system is provided for generating a visualization of a lung fissure. The system includes a medical scanner, an image processor, and a display. The medical scanner is configured to acquire medical imaging data representing at least two adjacent lobes of a lung. The image processor is configured to generate a mesh of a boundary of at least two adjacent lobes from the medical imaging data and to identify in the medical imaging data, fissure image data representing the lung fissure between the two adjacent lung lobes. The image processor is further configured to augment the mesh with the identified fissure image data and render a two-dimensional image with the augmented mesh projected onto a plane. The display is configured to display the rendered two-dimensional image.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION

Embodiments provide a method and system for generating a two-dimensional visualization of a region that directly shows lung imaging data and shows where a lung fissure is complete or incomplete. The visualization approach also provides a view for identifying if any incompleteness is clustered or otherwise located in one region. The information provided by the view may be useful in analyzing and determining a treatment for different lung diseases. The view may be a singular view showing the lung and fissure completeness.

To generate the visualization, image slices from a computed tomography system are acquired as medical imaging data. A mesh is generated from the medical imaging data. Fissures are identified in the medical imaging data. The mesh is updated with data from the identified fissures. Vertices in the updated mesh are projected into a straight plane. The resulting two-dimensional image may be presented as a singular view of the fissure to be examined by a user.

Figure 1:
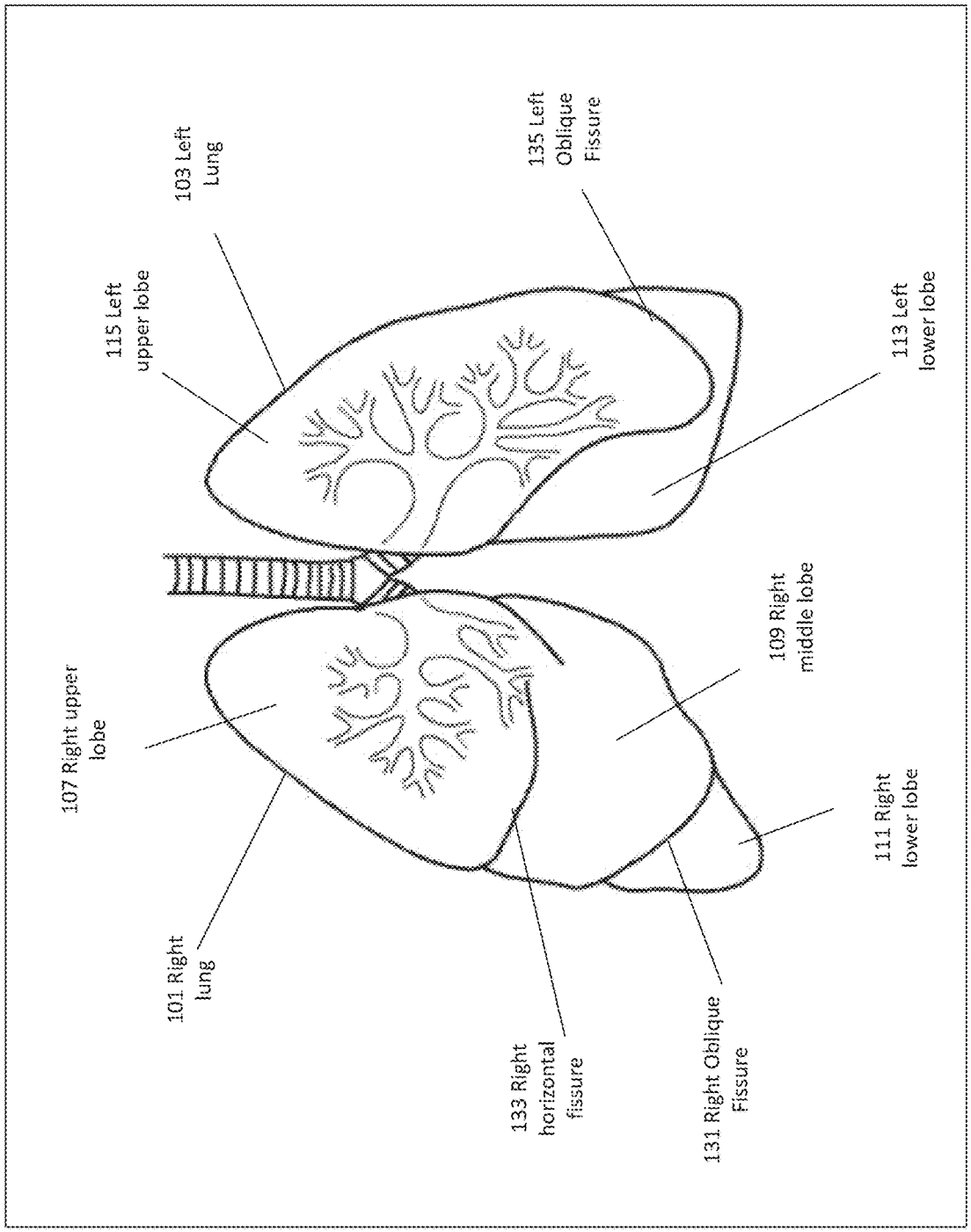
FIG. 1 depicts an example of a lung and lung lobes.

As depicted in FIG. 1, a lung includes a left lung 103 and a right lung 101. By convention, the lungs are depicted as if viewing the patient from the front, so the left lungs are on the right side of the image and vice versa. The left 103 and right lungs 101 are each divided into a plurality of lobes by deep clefts that are referred to herein as fissures. The outer surface of the lungs is lined by pleura, including an inner layer that is the visceral pleura that dips into the fissures to surround the lobes. The fissures are the space between the lobes of the lung and are defined by the outermost surface of the lobes and the visceral pleura at the locations where the lobes touch each other. Although the fissure is a space between abutting lobes, the fissure is also a very thin layer of tissue surrounding the fissure that may be detected on a volumetric image. The right lung 101 normally includes three lobes (the upper 107, middle 109, and lower 111 lobes) that are divided by two fissures, e.g. the oblique 131 and the horizontal 133 fissures. The left lung 103 normally includes two lobes (the upper 115 and lower 113 lobes) with one fissure, the oblique fissure 135, between the two lobes.

The edges of the lobes and the pleura that lines the lobes define the fissures and separate the lobes such that the ventilation of each lobe is separate from that of adjacent abutting lobes. In addition, the pleura normally forms a smooth surface, allowing abutting lobes to slide relative to each other during inhalation and exhalation. However, in certain disease conditions, the pleura may become thickened or adherent. In addition, abutting lobes may adhere to each other and the pleura and lung margins that normally define the fissure may be lost. In such locations, the fissure is described as "incomplete," "missing," or "absent" and air may flow between the lobes. For a medical imaging scan such as CT, the fissures may be identified in images slices (e.g., images of 2D planes) using known imaging techniques. The image slices, however, are incomplete as the slices are unable to depict the entirely of the fissure as the fissures exist in three-dimensional space.

Current approaches for analyzing and diagnosing lung fissures require a technician or surgeon to view multiple two-dimensional slices. The technician or surgeon then may make a determination of whether the lung fissure is complete by looking back and forth between the slices and visually comparing the image data. The method is subject to human error, tedious, and potentially inaccurate. In another approach, a three-dimensional model is generated that includes a three-dimensional representation of the lung including the fissures. Similar to the two-dimensional method, the approach requires user interaction, as the view has to be rotated and manipulated to get an optimal view of the anatomy of interest. Certain portions of the lung may be difficult to view due to other tissues or complex interactions. The methods and manipulations may be time consuming for the user, especially for less experienced users. Therefore, a method that determines the best view without user interaction is highly desirable.

Figure 2:
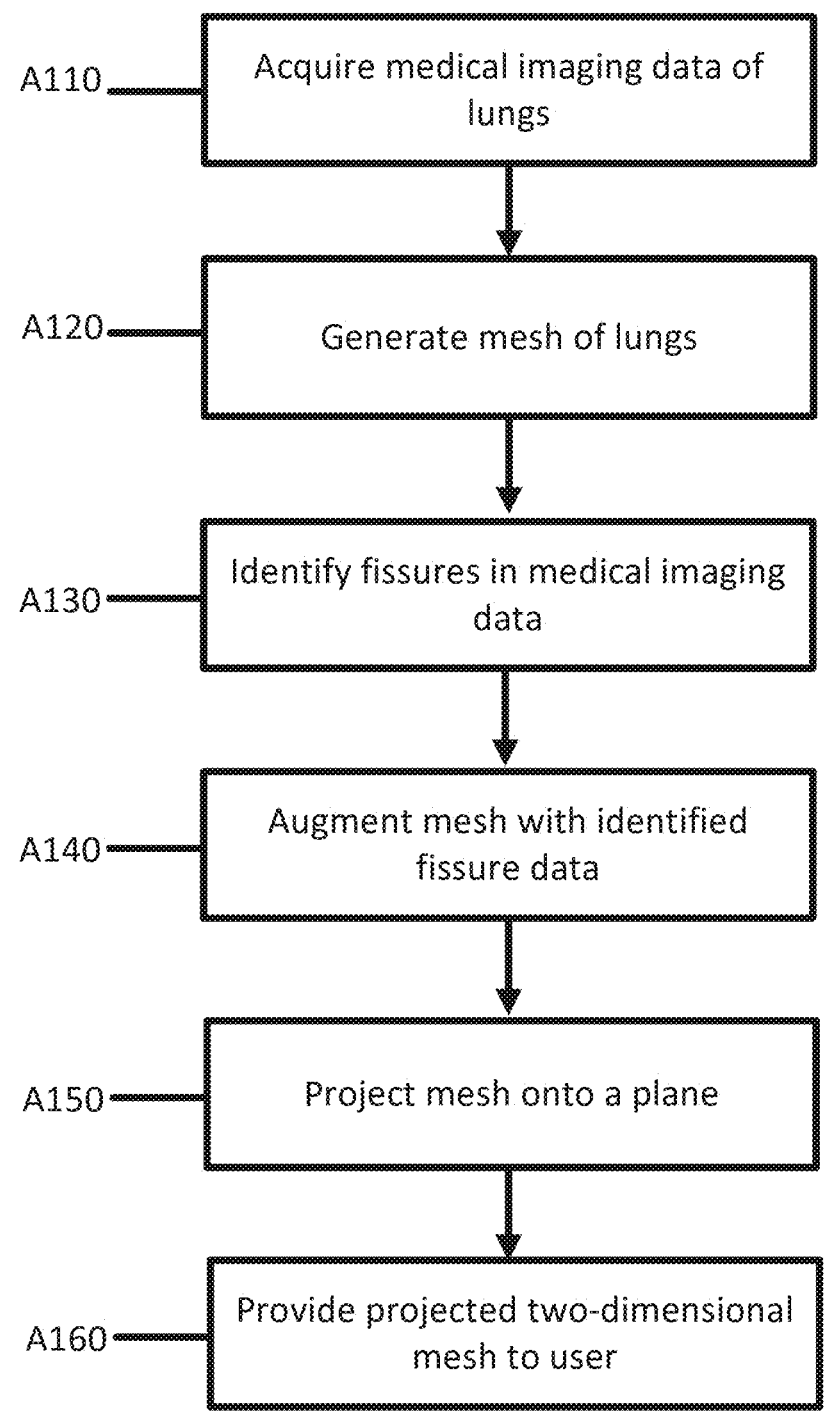
FIG. 2 depicts an embodiment of a method for generating a visualization of a lung fissure.

FIG. 2 depicts one embodiment of a method for generating a visualization of a lung fissure. The method for visualization generates a concise two-dimensional image of a region that directly shows the imaging data and where the fissure is complete or incomplete. Lung fissures and lobes may be examined during a diagnosis and/or therapy of different lung diseases. The visualization approach also allows one to see if any incompleteness is clustered or otherwise located in one focal or particular region.

Figure 8:
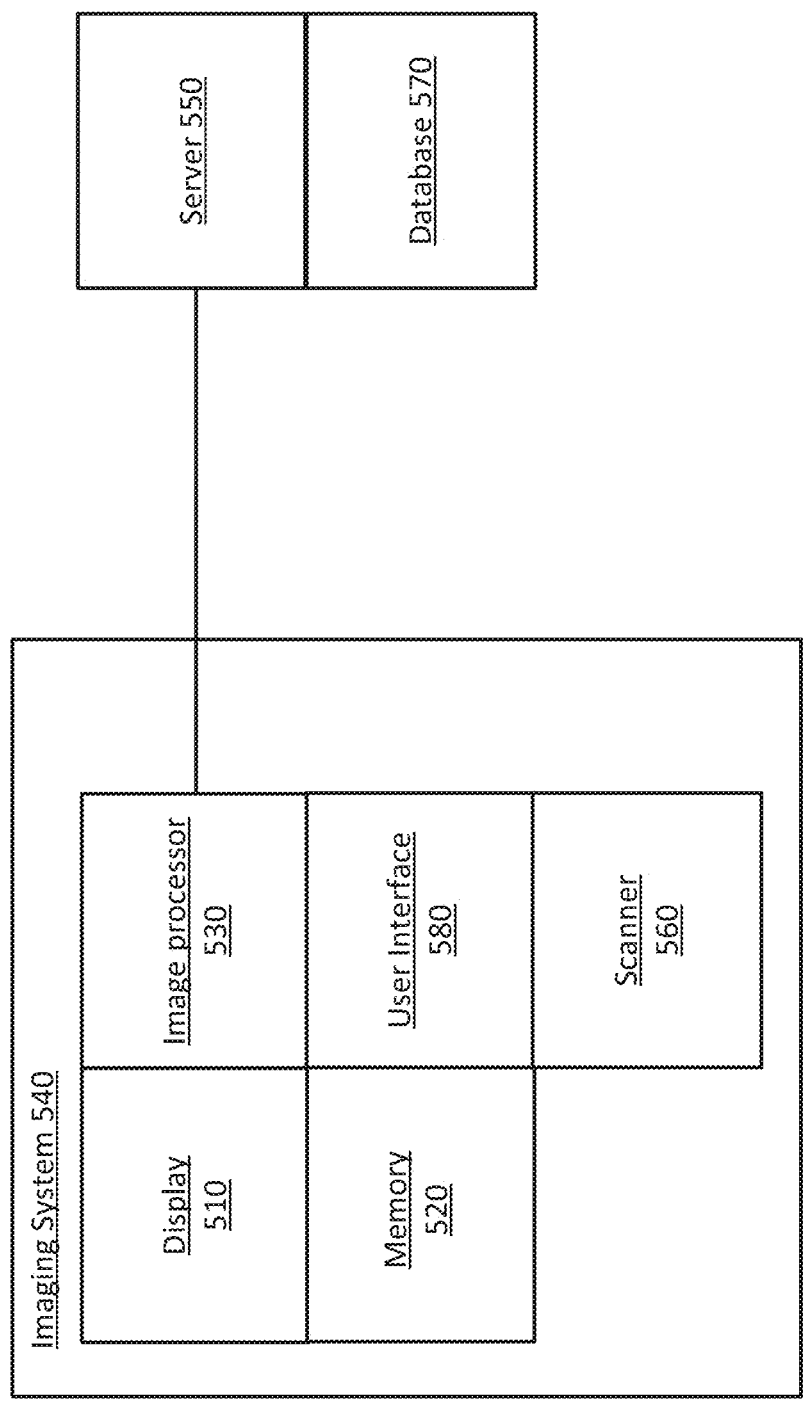
FIG. 8 depicts an embodiment of a system for generating a visualization of a lung fissure.

The acts are performed by the system of FIG. 8, other systems, an image processor, a medical scanner, a workstation, a computer, and/or a server. For example, A110 may be performed by a medical imaging device or medical scanner. The other acts are performed by a processing component, such as an image processor, medical scanner, a workstation, a cloud-based processing computing node, or simply a computer. Additional, different, or fewer acts may be provided. The acts are performed in the order shown (e.g., top to bottom) or other orders.

At act A110, a medical imaging device scans the lungs of a patient. Herein, plural lungs and fissures are used, but a single lung and/or fissure may be used. The medical scanner generates imaging data representing a patient. The image or imaging data is made available by or within the medical imaging device. Alternatively, the acquisition is from storage or memory, such as acquiring a previously created dataset from a picture archiving and communication system (PACS). A processor may extract the data from a picture archive communications system or a medical records database.

The imaging data or the medical image is data representing a two-dimensional slice or a three-dimensional volume of the patient. The data may be in any format. While the terms image and imaging are used, the image or imaging data may be in a format prior to actual display of the image. For example, the medical imaging data may be a plurality of scalar values representing different locations in a Cartesian or polar coordinate format different than a display format. As another example, the medical image may be a plurality red, green, blue (e.g., RGB) values output to a display for generating the image in the display format. The medical image may be currently or previously displayed image in the display or another format. The imaging data is a dataset that may be used for imaging, such as scan data or a generated image representing the patient.

Any type of medical imaging data and corresponding medical scanner may be used. In one embodiment, the imaging data is a computed tomography (CT) image acquired with a CT system. For example, a chest CT dataset may be acquired by scanning the lungs. The output image may be a two-dimensional image slice. For a three-dimensional CT image, the raw data from the detector is reconstructed into a three-dimensional representation. As another example, magnetic resonance (MR) data representing a patient is acquired with an MR system. The data is acquired using an imaging sequence for scanning a patient. K-space data representing an interior region of a patient is acquired. Fourier analysis is performed to reconstruct the data from the k-space into a three-dimensional object or image space. The data may be ultrasound data. Beamformers and a transducer array scan a patient acoustically. Received acoustic signals are beamformed and detected into polar coordinate ultrasound data representing the patient.

The medical imaging data represents tissue and/or bone structure of the patient. For imaging the lungs, the imaging data may include response from the lungs and the anatomy around the lungs (e.g., upper torso). In other embodiments, the medical image represents both function (such as perfusion) as well as structure, such as nuclear medicine (NM) data.

The medical imaging data represents a two or three-dimensional region of the patient. For example, the medical imaging data represents an area or slice of the patient as pixel values. As another example, the medical imaging data represents a volume or three-dimensional distribution of voxels. The three-dimensional representation may be formatted as a stack or plurality of two-dimensional planes or slices. Values are provided for each of multiple locations distributed in two or three dimensions. The medical imaging data is acquired as one or more frames of data. The frame of data represents the scan region at a given time or period. The dataset may represent the area or volume over time, such as providing a 4D representation of the patient.

Figure 3:
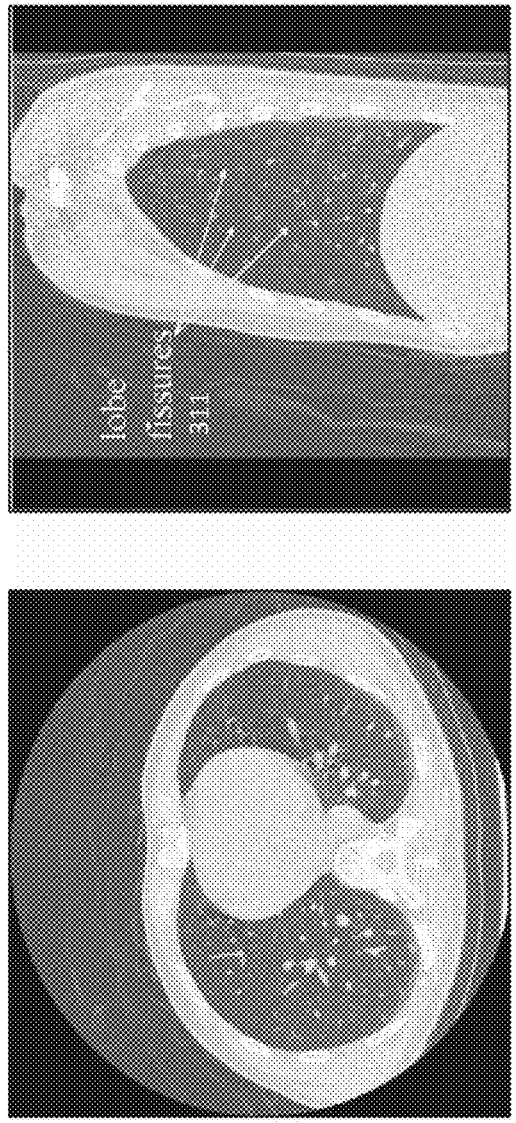
FIGS. 3A and 3B depict example CT scan images of a lung.

FIGS. 3A and 3B depicts example CT scan images of a lung. FIG. 3A is a transverse slice of both lungs. Due to the orientation, fissures 311 are difficult to identify in the CT image. FIG. 3B depicts a sagittal slice of one lung. In FIG. 3B, the lobe fissures 311 may be identified with difficulty as the bright white lines that dissect the lobe. However, due to the visualization, an operator may not be able to determine if a fissure 311 is complete or incomplete.

At act 120, a mesh of the lobes of the lungs is generated. The mesh includes interconnected nodes defining an anatomical surface. The mesh is a three-dimensional construct, such as representing a three-dimensional surface or anatomy. The mesh may include voxels that define the boundaries between the different lobes of the lung. The boundaries may be representative of locations of or near the lung fissures. Different techniques may be used to generate the mesh. In an embodiment, a segmentation algorithm may be used to initially separate the lungs from other tissues or organs in the medical imaging data. The bronchial tree and vessels are segmented and identified. The boundaries of the lobes are identified based on the bronchial and vessel tree. The mesh is generated from the boundaries.

The medical imaging data may be three-dimensional imaging data, represented, for example, by voxels. The three-dimensional imaging data may be generated by combining a plurality of two-dimension image slices acquired at act A110. The mesh may be generated by processing the image data to identify voxels that represent the boundaries of the lobes and as such, the fissures. Image voxels belonging to air-filled anatomies are identified in the medical imaging data. Techniques such as using a fixed threshold or histograms may be used to identify the air-filled image voxels. In addition, voxels relating to unconnected structures or organs such as the stomach or parts of the intestine may be ignored or removed. The remaining image data includes data that represents the lung including the one or more lobes. In an embodiment, the image data may be preprocessed so that tissue data belonging to other organs, for example, may already be removed.

In the remaining image data, the bronchial tree of the lung may also be segmented. A trachea may be identified in the image data set using known techniques. For example, as there is a relatively high contrast between an airway lumen and an airway wall. One method of identifying the trachea includes using a three-dimensional region-growing procedure. The trachea may be used as a seed point for a segmentation of the bronchial tree. Due to partial volume effects, the best threshold may differ from the air value of −1000 Hounsfield units (HU). In the case of thinner bronchi, an adaptive value may be adjusted according to the bronchial diameter.

Once the bronchial tree is segmented, the bronchial tree may be reduced to a skeletal model, e.g. a series of lines. The bronchial tree and branches are identified from the skeletal model. For example, the carina that is the branch point between the right and left lung, as well as the next order branch points for the mesh into the lobes, are identified. The bronchial tree may be limited to the main bronchi and a fixed number of branches. The branches may be counted in the skeletonized tree, or by limiting the diameter of the bronchi.

Referring back to the image voxels of the lung, the air-filled voxels belonging to both the lung tissue and the bronchi are determined. The bronchi identified may be ignored. The residual voxels belong to the lung parenchyma. The vessels of the lung may be segmented from the non-air voxels. Different techniques may be used, such as region growing. Additionally, the bronchial tree may be used to identify the arteries as the arteries may be in most cases parallel to the bronchi. Further, a three-dimensional distance measurement may be used for the identification. The applied algorithms may ignore single voxels and define the single voxels as not belonging to the anatomy to be segmented. Algorithms such as "closing" can be used to re-assign single voxels or small groups of voxels to the volume to be segmented.

The vessel segmentation may be improved if the vessels are enhanced with intravenously applied contrast material. However, even when contrast agent is absent, vessel segmentation may proceed as there is a sufficient difference in HU values between larger vessels and parenchymal tissue for a portion of the vessel tree to be segmented.

In an embodiment, only the main vessels of the lobes are segmented and identified. The skeletonizing of the vessel tree provides the assignment of vessels to the lung, the lobes, and additionally segments and sub-segments. Similar to the bronchial tree, the extent of the vessel tree may be limited to a particular size or number of vessel branches.

Using the bronchial tree and vessel tree, voxels may be assigned to the five lung lobes. The three-dimensional distances to the neighboring airways and vessels are calculated. The airway/vessel pair with the lowest distance defines the anatomy and the assignment to one of the five lobes. The assignment to the 5 lobes may take place even in patients where the fissure is not visible, as the lobar boundaries are anatomically defined by the bronchial tree. Voxels belonging to different lobes help define the surface of the lobes and are used to create the mesh. Certain voxels may be removed or smoothed as the lobar divisions are known to be curved plane-like surfaces without any discontinuities. Outlier voxels that differ extremely from neighboring voxels may be shifted to an anatomically plausible position or removed.

At act A130, fissures are identified in the imaging data. Image pixels or voxels that represent fissures may be identified in the original unprocessed (unsegmented) imaging data. Image pixels or voxels of fissures have higher HU values than neighboring voxels or pixels. In an embodiment, to limit the search, a search region is defined around the mesh generated at act A120. Boundary vertices of the mesh are defined. On both sides of the boundaries, at a predefined distance, new search vertices are set. The search vertices on each side define two surfaces in front of and behind the original surface, the region therebetween representing the search region.

Within the search range, an edge detection is performed. Different techniques such as algorithms based on the eigenvalues of the Hessian matrix or a watershed algorithm may be used. The eigenvectors of the Hessian matrix of each voxel may be analyzed to measure if a voxel belongs to a locally plate-like object with bright appearance (e.g. a fissure). In CT images, for example, the fissures may be highlighted with a bright appearance. In an example, in CT images of 1-3 mm thickness, the fissure may often be identified as a thin curve with high attenuation values compared to the surrounding tissues. The fissure may also be identified using different methods such as machine learning algorithms to separate the pixels or voxels that represent the fissures. Other techniques such as watersheds, level-sets, graph optimization as well as atlas- and multi-atlas registration may be used.

At act A140, the mesh is augmented with the identified fissure data. The found fissures in act A130 may differ from the previously found surfaces of the mesh of act A120. For example, the mesh of act A120 defines the boundaries of the lobes and as such only estimates the locations of where the fissures may be located. The mesh may assume a fissure where there is none or an incomplete fissure. The found fissures of A130 are actual voxels that correspond to the actual locations of the fissures as depicted in the medical imaging data. The combination of the found fissures and the mesh may provide an accurate depiction of the fissures or lack thereof.

In an embodiment, the medical imaging data is registered to the mesh during the mesh generation/segmentation process in A120. There are three potential possibilities when comparing the mesh with the identified fissures data. In an example, a voxel in the mesh that is labeled as a fissure may either be verified by the identified fissures data, marked as lacking (e.g. incomplete), or identified as misplaced. In the first scenario, the mesh voxel may be labeled as a fissure. In the second scenario, the mesh voxel may be labeled as the location of an incomplete or missing fissure. In the third scenario, known algorithms may be run to match the mesh voxel to the correct fissure voxel. The vertices of the mesh may be shifted to the new position as described in the found fissures. Certain voxels that are outliers in the found fissures may be ignored. For example, if a voxel is outside a threshold range of the mesh, the voxel may be ignored as the fissures are curved plane-like surfaces.

In an embodiment, the shifted vertices due to found fissures are marked for the visualization. When projected and visualized, the shifted vertices may be easily identified by using, for example, different colors or transparencies. Similarly, the points on the mesh that correspond to incomplete or missing fissures may also be marked for visualization.

Figure 4:
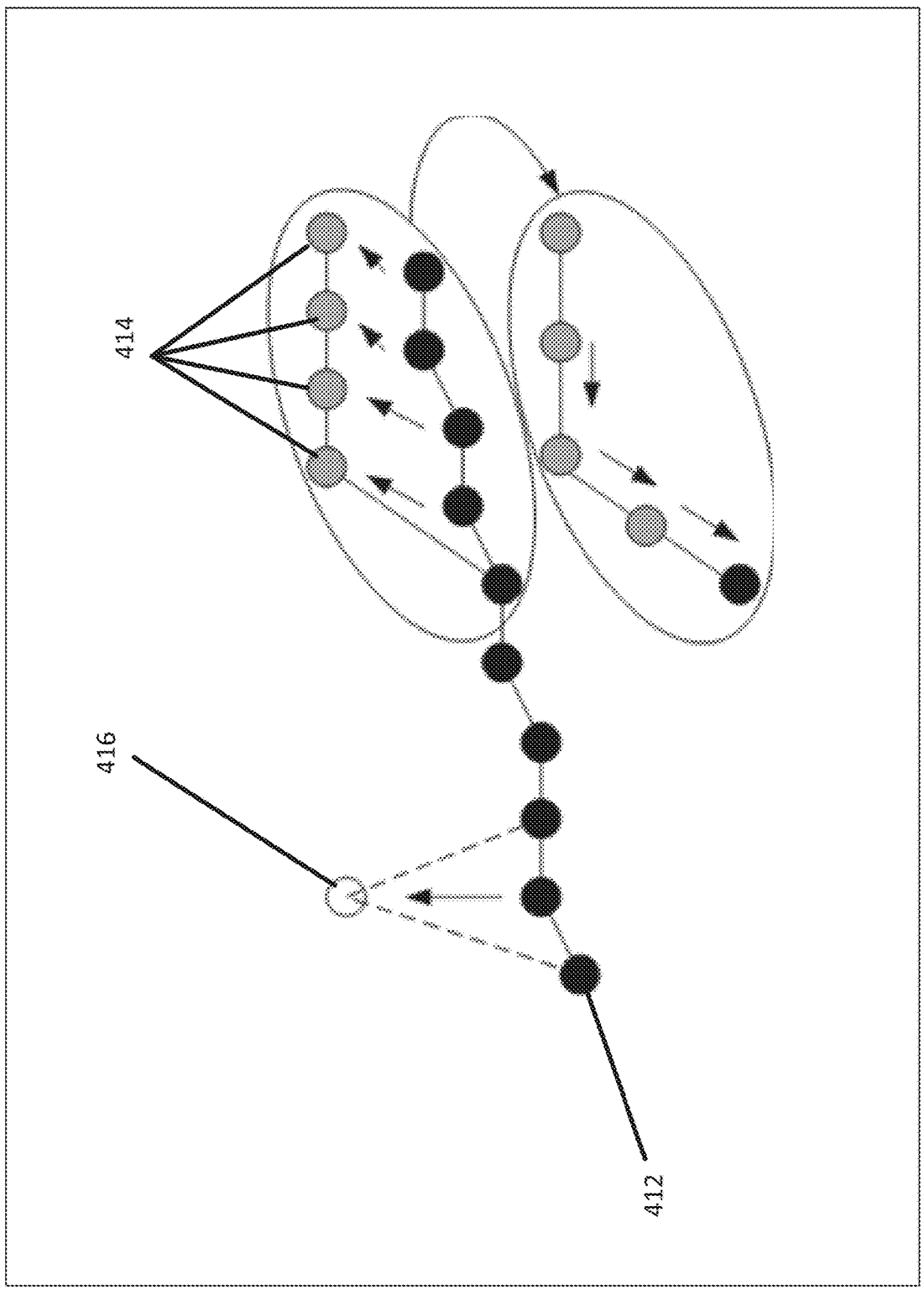
FIG. 4 depicts an adjustment of the vertices of the mesh according to an embodiment.

FIG. 4 depicts an adjustment of the vertices of the mesh. The mesh voxels/vertices 412 are depicted as solid black circles. The identified fissure voxels 414 are depicted as grey circles. FIG. 4 also depicts an outlier fissure voxel 416 The mesh and fissure voxels in FIG. 4 have been simplified to two dimensions. To augment or adjust the mesh, the two sets of voxels are compared against one another. If the voxels match up, no changes will be made. The mesh voxels may be labeled as verified. If the voxels do not match up, for example on the left side of FIG. 4, an attempt is made to reconcile the discrepancies. In the example depicted, the outlier fissure voxel 416 may be discarded if the outlier fissure voxel 416 is determined to be an error. Fissures tend to take the form of a curved plane. Adjusting the mesh to include the outlier would disrupt the curved plane beyond a threshold amount and would be unnatural. As such, the outlier fissure voxel 416 may be discarded. On the right side of FIG. 4, there is also a discrepancy between a voxel in the mesh and voxels in the identified fissure data. As there is a series of voxels, the fissure data may be determined to be correct. The mesh voxels are shifted to incorporate the new voxels. The mesh may alter the locations of the voxels to maintain its curved structure.

At act A150, the vertices of the mesh are projected onto a plane. A projection point is selected. The projection point is a location from which the fissure is to be viewed. The projection point may be automatically selected or may be manually selected. The projection point may be different for each lobe or fissure. In an embodiment, there are multiple different selectable projection points presented to a user for selection. A user may select from the different projection points to view different visualizations of the fissures.

In addition to the projection point, a plane is also defined. The plane may be a straight or flat plane or a curved plane. A straight or flat plane is a two-dimensional plane that is located behind the fissure from the point of view of the projection point (e.g. no point of the fissure may be located further away than the plane from the projection point). The straight plane may be defined automatically or manually selected. Different straight planes may be paired with different projection points to provide different preset visualizations for different lobes or fissures.

In an embodiment, a curved plane may be used in place of the straight plane. A curved plane may provide less distortion at the edges of the projection. The curvature of the plane may be selected automatically or adjusted manually. The curvature and placement of the curved plane may be selected as a function of the fissure and the projection point.

Figure 5:
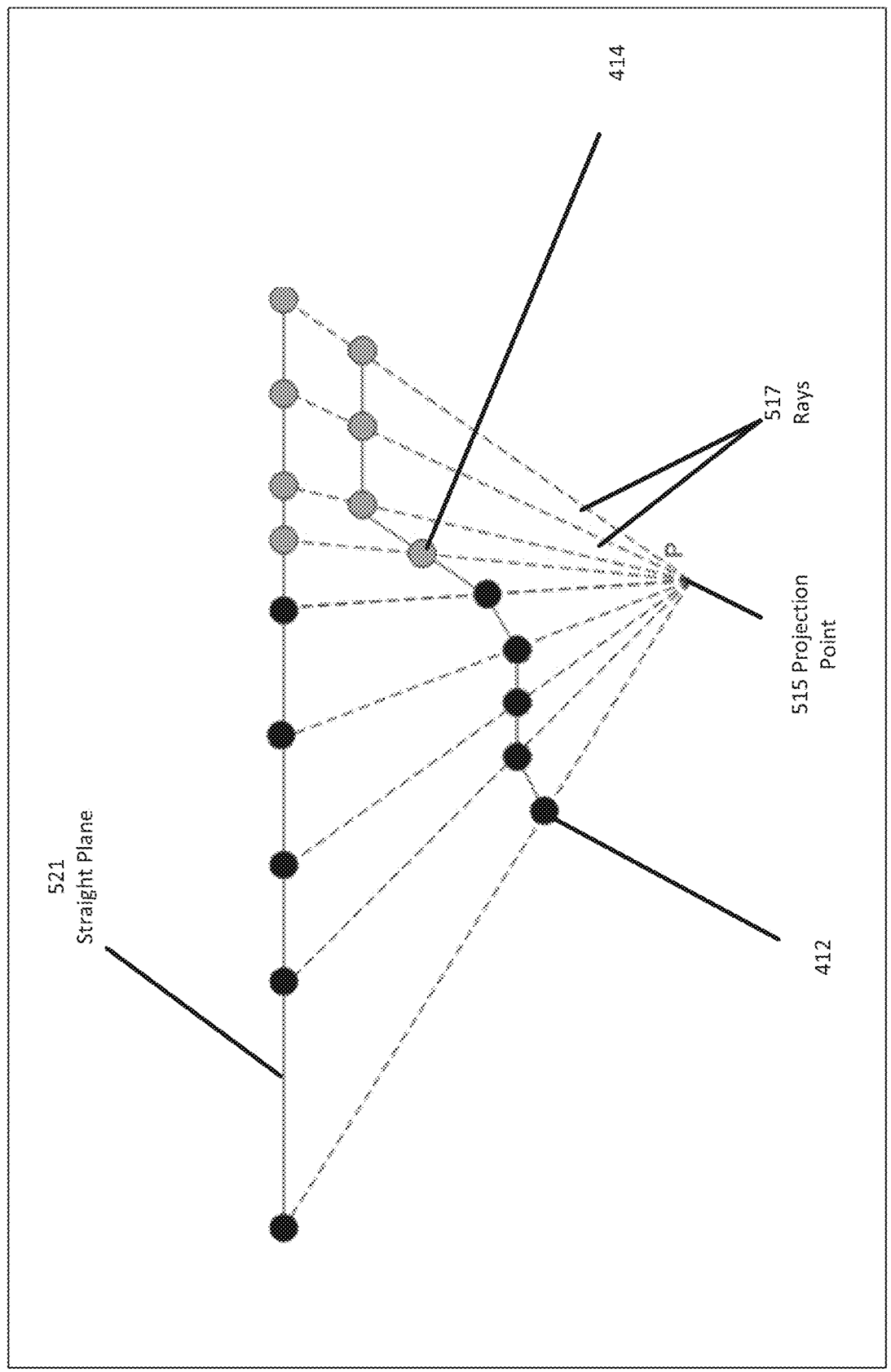
FIG. 5 depicts the transfer of voxels of the augmented mesh into a straight plane according to an embodiment.

FIG. 5 depicts the transfer of voxels of the augmented mesh (e.g. fissure surface) onto a straight plane. From the projection point 515, rays 517 are defined going through the mesh voxels (412, 414) into a selected plane 521. The projections of the voxels (412, 414) in the resulting straight plane 521 may result in unequally distributed points on the plane that may be interpolated or spatially filtered to get equidistant points. Identified fissures voxels 414 that are fissure points that were detected in act A140 and not just on the separation between lobes may be displayed in a different color (here grey). Alternative methods for projection may be used. For example, a projection algorithm may be used to limit distortions at the edge of the plane 521.

At act A160, the projection of the mesh is provided to a user. The projection may be rendered by an image processor into a two-dimensional image. In an embodiment, multiple two-dimensional images may be presented to an operator, for example, images of each of the fissures of a patient. Different visualizations may be provided, for example with different highlights or different features included.

Voxels or pixels representing the fissures may be displayed in a color-coded visualization. Different colors or visual indicators may be used to indicate the existence or the absence of the fissure. For example, each of the voxels that were identified as found fissures may be colored green. For each of the mesh voxels that there was not an associated found fissure voxel, the resulting pixel on the projection may be colored red. An altered voxel may be colored a different color. A user, e.g. radiologist may recognize how an incomplete fissure may affect the planned intervention. For example, together with the bronchial tree, the visualization may show if side ventilation of the tissue after a bronchial valve placement may occur.

Alternatively, a destination-driven algorithm may be used. From equidistant points of the straight plane, rays are drawn to the projection point 515. The rays may not hit the fissure vertices. A strong distortion, for example, at the outer borders of the plane may be eliminated by using parallel projections. This is beneficial for fissure surfaces with low curvature. Distortions caused by the applied interpolation algorithms are acceptable, as the distortions are not clinically significant to the task of determining fissure completeness.

The bronchial tree and the vessel tree may similarly be projected into the straight plane used for the fissure visualization. Fissures, bronchi, and vessels as such may be displayed together, with different transparencies and different colors to help with analysis and diagnosis. Displaying and rendering the image may be done using a cinematic renderer to provide a more detailed and realistic visualization. Vessel segmentation or filters may also be used to better highlight vessels.

In an embodiment, only the bronchi and vessels near to the fissure are projected and visualized. A pre-defined distance may be selected (automatically or manually). The restriction to a pre-defined distance provides that only the anatomies of most interest are displayed.

In an embodiment, one or all of the three fissures may be depicted in a single view. Each fissure may be visualized with a planar image. For the left lung, the fissure between upper and lower lobe is visualized; for the right lung, the two fissures between upper and middle lobe, and between middle and lower lobe, are shown. Alternatively, each fissure may be presented to a user individually.

In another embodiment, an image is provided that does not visualize the fissure plane directly but only a part of the lung tissue that is affected by a leakage. The image voxels inside the lung segment are color-coded and displayed in orthogonal MPRs or in VRTs of the complete lungs (left and right together), in one of the lungs (only left or only right), or in just one lung lobe.

Color coding of voxels may be applied in different ways. One method is to assign one color to found fissures and a different color to the lobe separations that are not part of the found fissures. Another color coding scheme may be to simulate leakage. Voxels inside each lobe may be set to a lobe-specific color, e.g. red for the upper left, green for the lower left lobe, etc. Voxels next to separations without found fissures (leaks) may be set to a combination of the two colors, for example, depending on the distance to the leak.

Figure 6:
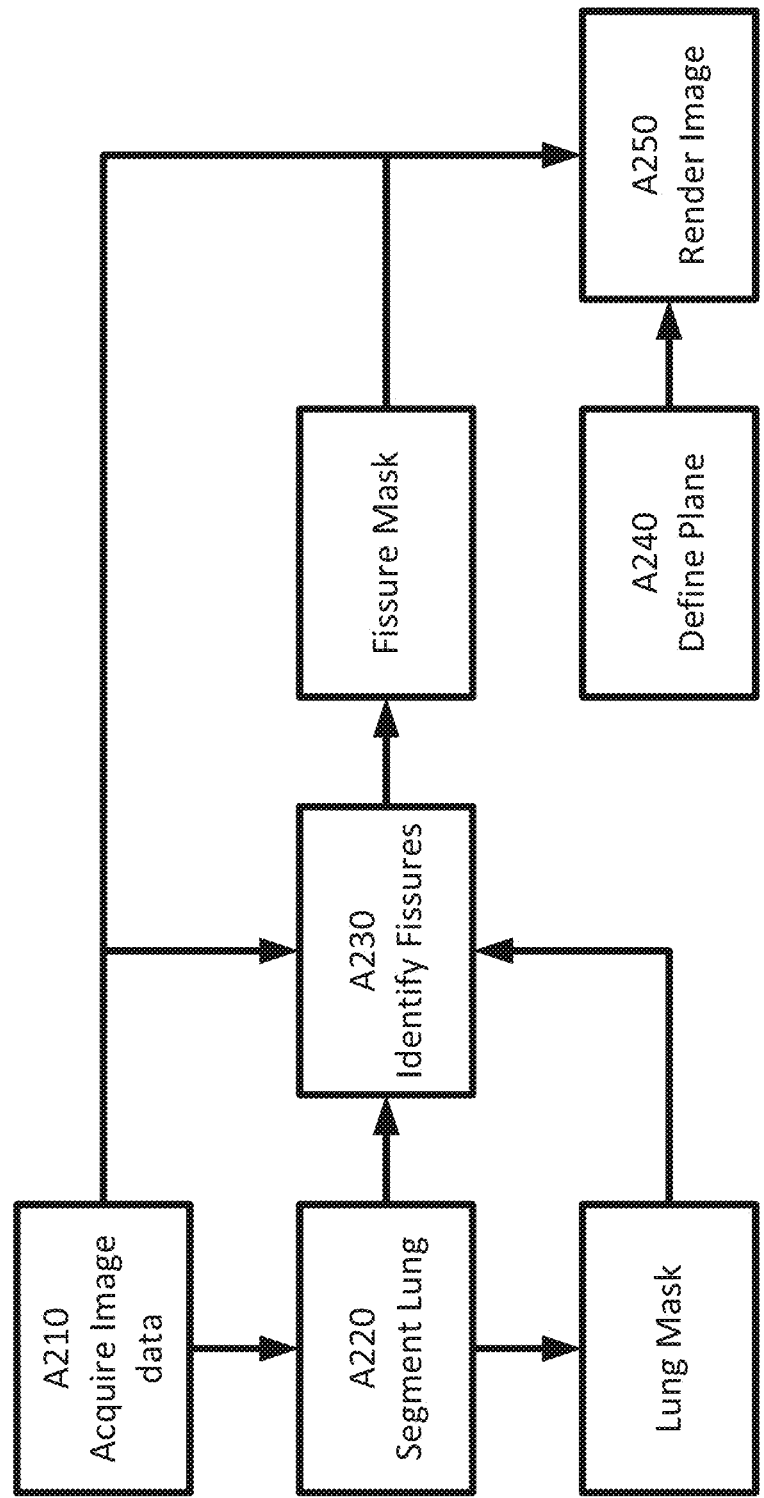
FIG. 6 depicts an embodiment of a method for generating a visualization of a lung fissure.

FIG. 6 depicts an embodiment of a method for generating a visualization of a lung fissure. Lung image data is identified. Fissure image data is detected. A point of view is identified for the lung fissure. An image is rendered with the lung image data and fissure image data from the point of view.

The acts are performed by the system of FIG. 8, other systems, a medical scanner, a workstation, a computer, and/or a server. For example, acts A220-A240 are performed by a processing component, such as a workstation or a computer. Act A210 may be performed by a medical scanner or imaging device. The acts are performed in the order shown (e.g., top to bottom) or other orders. Acts A220 and A230 may be performed in any order or simultaneously. Additional, different, or fewer acts may be used, such as not performing A210 if the imaging data has been previously acquired from an imaging device.

At act A210, image data for a lung region is acquired. The medical scanner generates imaging data representing a patient. The image or imaging data is made available by or within the medical imaging device. Alternatively, the acquisition is from storage or memory, such as acquiring a previously created dataset from a picture archiving and communication system (PACS). A processor may extract the data from a picture archive communications system or a medical records database.

The data may be in any format. The medical imaging data represents tissue and/or bone structure of the patient. For imaging the lungs, the imaging data may include response from the lungs and the anatomy around the lungs (e.g., upper torso). In other embodiments, the medical image represents both function (such as perfusion) as well as structure, such as nuclear medicine (NM) data.

The medical imaging data represents a two or three-dimensional region of the patient. For example, the medical imaging data represents an area or slice of the patient as pixel values. As another example, the medical imaging data represents a volume or three-dimensional distribution of voxels. The three-dimensional representation may be formatted as a stack or plurality of two-dimensional planes or slices. Values are provided for each of multiple locations distributed in two or three dimensions.

At act A220, the image data is segmented to identify and separate the left and right lungs generating a mask for each of the left and right lungs. Any approach may be used. In an example, the lung data is identified using a classification technique. A thresholding method may be used to identify each region based on the density distribution. A three-dimensional region growing method may be used to trace the airways of the bronchus. From a seed point selected automatically, a three-dimensional region growing method is applied to identify the whole airway region from the image data. The airway region is separated into a tree structure using branch by branch analysis. After deleting the airway region and the air regions with a small volume, the remainder is regarded as lung data. The lung data are separated into left and right lungs. The lung data is smoothed using a morphological filter. The hole inside the smoothed initial lung data is filled. The other tissue regions lacking air within the lung data is vessels data. A three-dimensional region growing method is used refine the vessel data and then identify the final lung vessels by deleting the bronchial walls from the lung data based on the distances from the surface of airways. The lung vessels are further divided into five lobar groups based on the distance to each lobar bronchial tree. The bronchus and vessels are classified into the five lobar groups. Each voxel of the lung data is classified into a lung lobe for the "skeleton" that is nearest to the voxel. Alternative method or techniques may be used to segment the image data into the lungs. The output of the segmentation is a lung mask that specifies the pixels/voxels that represent the lung lobes.

At act A230, fissures are detected in the image data. The fissures may be identified using the segmented lungs of A220 (e.g. the lung mask and the bronchial/vessel data). Due to the accuracy of lung vessel and bronchi extractions, the positions of initial fissures may have a small shift comparing to the real fissures in many cases. The identification of the fissures may be performed by detecting edges based on density distribution in the image data and selecting the surface pattern around initial fissures as the final fissures. In an embodiment, a fissure filter (deep learning based or otherwise) is applied to the lung region to detect the fissures. The output of fissure detection is a fissure mask that specifies voxels that represent the fissure in the image data.

At act A240, a point of view is defined for one or more of the three fissures. The point of view may be defined by selecting a plane for each fissure. The plane may be identified based on the expected fissure location. The plane is used to position the camera for rendering purposes below at act A250. A camera position, e.g. point of view, may be defined to capture the entire surface of the plane in a predefined image size. Each fissure may include one or more planes that define different views. Each plane may, for example, define a mask for rendering the image of the fissure as a result of the field of view of the camera.

Figure 7C:
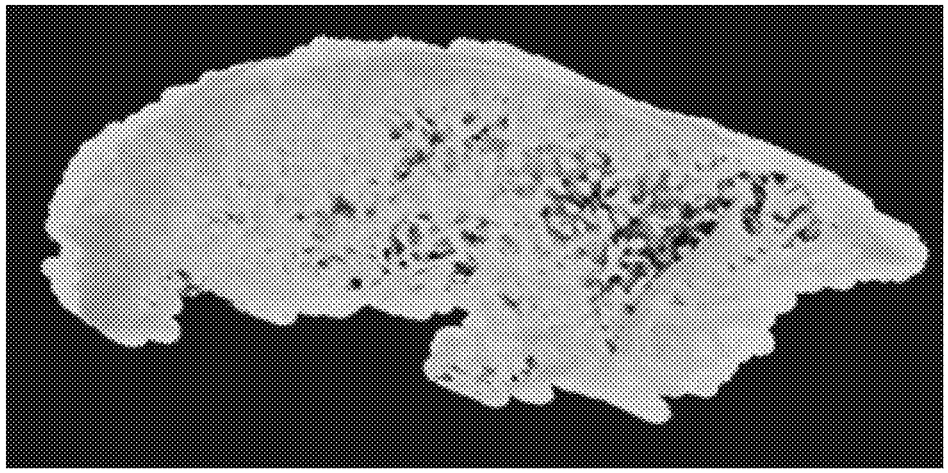
FIG. 7 depicts example rendered images of the method of FIG. 6.
Figure 7B:
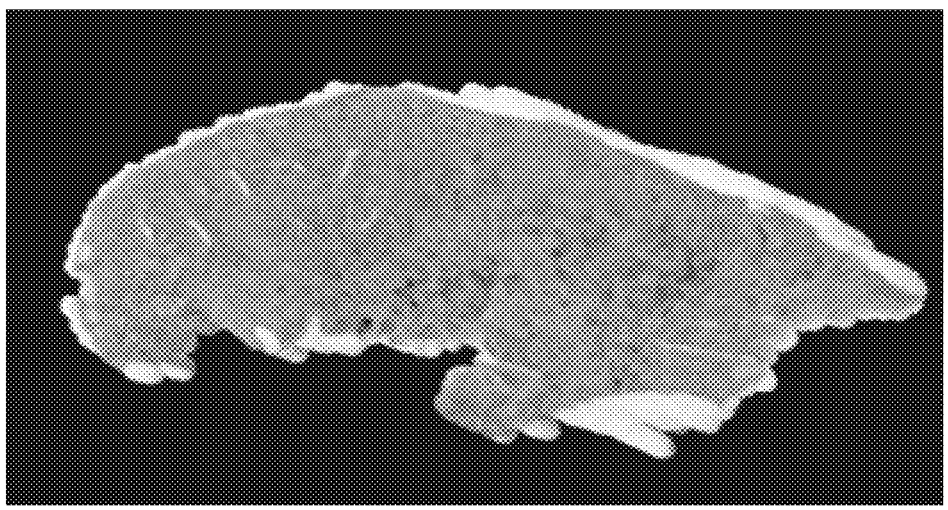
Figure 7A:
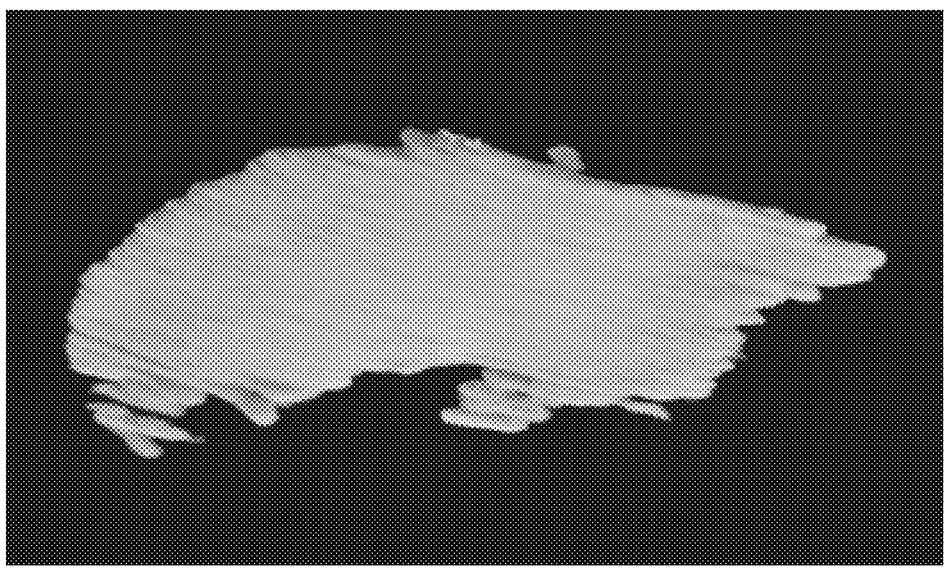

At act A250, an image is rendered of the fissure data. The image may include the image data specified by the lung data, the fissure data, or both. The image is rendered from the selected point of view. FIGS. 7A, 7B, and 7C depicts examples of rendered images that result from the workflow of FIG. 6. Three different single-view renderings of the second proposed method applied to the left oblique fissure are depicted. The leftmost image in FIG. 7A depicts the raw output of the fissure filter. The view depicts that the fissure is complete with no localized holes. The middle and rightmost images, FIGS. 7B and 7C respectively, depict the rendered lung data. The vessels and regions within the lung data are depicted in FIGS. 7B and 7C.

In an embodiment, the image includes both the image data that from the lung data and the fissure data. The lung and fissure data may include different visual indicators so that a user may quickly detect where the fissure is complete or incomplete. For example, if the fissure data may be overlaid on top of the lung data so that when viewed, gaps or holes in the fissure data may show the underlying lung data and as such indicate an incomplete fissure.

FIG. 8 depicts an embodiment of a system for generating a visualization of a lung fissure. The system includes an imaging system 540, a server 550, and a database 570. The imaging system includes an image processor 530, a memory 520, a display 550, and a scanner 560. Additional, different, or fewer components may be provided. For example, network connections or interfaces may be provided, such as for networking with a medical imaging network or data archival system. In another example, the user interface 580 is provided as part of the display 510 or imaging system 540. In yet other embodiments, the server 550 and/or database 570 are not provided.

The image processor 530, memory 510, display 510, user interface 580, and scanner 560 are part of the imaging system 540. Alternatively, the image processor 530 and memory 520 are part of an archival and/or image processing system, such as associated with a medical records database workstation or server, separate from the imaging system 540. In other embodiments, the image processor 530 and memory 520 are a personal computer, such as desktop or laptop, a workstation, a server, a network, or combinations thereof. The image processor 530, display 510, and memory 520 may be provided without other components for acquiring data by scanning a patient.

The imaging system 540, image processor 530, memory 520, display 550, user interface 580, and scanner 560 are provided at a same location. The location may be a same room, same building, or same facility. The devices are local relative to each other and are remote to the server 550. The server 550 is spaced apart by a network by being in a different facility or by being in a different city, county, state, or country. The server 550 and database 570 may be remote from the location of the imaging system 540.

The imaging system 540 is a medical diagnostic imaging system. Computed tomography (CT), X-ray, ultrasound, and/or magnetic resonance (MR) systems may be used. The scanner 560 may include a transmitter and includes a detector for scanning or receiving data representative of the interior of the patient. The imaging system 540 is configured to acquire image slices (2D) or an image volume (3D). The imaging system 540 may acquire a plurality of image volumes over time that may be used to generate a video.

In one embodiment, the imaging system 540 is a CT or X-ray system. An X-ray source connects to a gantry. A detector is also connected with the gantry opposite the X-ray source. The patient is positioned between the source and detector. The source and detector are on opposite sides of the patient and rotate and/or translate about the patient. The detected X-ray energy passing through the patient is converted, reconstructed, or transformed into data representing different spatial locations within the patient. In an embodiment, the imaging system 540 may include a portable or mobile C-arm. The C-arm includes an X-ray source and an image intensifier or flat-panel detector. The C-shaped connecting element allows movement horizontally, vertically and around the swivel axes, so that X-ray images of the patient may be produced from almost any angle. The generator emits X-rays that penetrate the patient's body. The image intensifier or detector converts the X-rays into a visible image displayed on a monitor or stored for later use.

In another embodiment, the imaging system 540 is an MR system. The MR system includes a main field magnet, such as a cryo-magnet, and gradient coils. A whole-body coil is provided for transmitting and/or receiving. Local coils may be used, such as for receiving electromagnetic energy emitted by atoms in response to pulses. Other processing components may be provided, such as for planning and generating transmit pulses for the coils and for receiving and processing the received k-space data. The received k-space data is converted into object or image space data with Fourier processing.

The memory 520 may be a graphics processing memory, a video random access memory, a random-access memory, system memory, cache memory, hard drive, optical media, magnetic media, flash drive, buffer, database, combinations thereof, or other now known or later developed memory device for storing data or video information. The memory 520 is part of the imaging system 540, part of a computer associated with the processor 530, part of a database, part of another system, a picture archival memory, or a standalone device.

The memory 520 stores medical imaging data, graphical or display setting, and/or images. The memory 520 may store data during processing for application and/or may store training data for a machine-learnt network 525.

The memory 520 or other memory is alternatively or additionally a non-transitory computer readable storage medium storing data representing instructions executable by the programmed image processor 530 for generating a visualization of a lung fissure. The instructions for implementing the processes, methods and/or techniques discussed herein are provided on non-transitory computer-readable storage media or memories, such as a cache, buffer, RAM, removable media, hard drive, or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code, and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The image processor 530 is a general processor, central processing unit, control processor, graphics processing unit, digital signal processor, three-dimensional rendering processor, image processor, application specific integrated circuit, field programmable gate array, digital circuit, analog circuit, combinations thereof, or other now known or later developed device for rendering a two-dimensional image from an image volume. The image processor 530 is a single device or multiple devices operating in serial, parallel, or separately. The image processor 530 may be a main processor of a computer, such as a laptop or desktop computer, or may be a processor for handling some tasks in a larger system, such as in the imaging system 530. The image processor 530 is configured by instructions, design, hardware, and/or software to perform the acts discussed herein.

The image processor 530 and/or server 550 are configured to perform the acts discussed above for generating a visualization of a lung fissure. The image processor 530 is configured to generate the visualization using lung mesh data and fissure data derived from imaging data acquired by, for example, the image scanner. The image processor 530 is configured to project the lung mesh/fissure data onto a plane to generate a two-dimensional view of the entirely of the fissure. The projection may be appended with additional information such as visual indicators of the bronchial or vessel tree, both of which may also be derived from the imaging data and projected onto the plane. The image processor 530 may be configured to generate a mesh of the at least two adjacent lobes from the medical imaging data and to identify in in the medical imaging data, fissure image data representing the lung fissure between the two adjacent lung lobes. The image processor 530 is further configured to augment the mesh with the identified fissure image data and render a two-dimensional image with the augmented mesh projected onto a plane. The image processor 530 is configured to render the two-dimensional image with a different color for mesh data that represents incomplete fissure points than mesh data that represents identified fissure image data.

The image processor 530 and/or server 550 are configured to provide the image volume to the display 510 or to the memory 520. The display 510 is a monitor, LCD, projector, plasma display, CRT, printer, or other now known or later developed devise for outputting visual information. The display 510 receives images, graphics, text, quantities, or other information from the image processor 530, memory 520, imaging system 540, and/or server 550. The display 510 is configured to provide image volumes to an operator.

The user interface 580 may be configured to receive one or more selections from a user. The user interface 580 may include an input device such as one or more buttons, a keypad, a keyboard, a mouse, a stylus pen, a trackball, a rocker switch, a touch pad, a voice recognition circuit, or other device or component for inputting data. The user interface 580 and the display 510 may be combined as a touch screen that may be capacitive or resistive.

The server 550 connects to the imaging system 540 via a network. The network is a local area, wide area, enterprise, another network, or combinations thereof. In one embodiment, the network is, at least in part, the Internet. Using TCP/IP communications, the network provides for communication between the image processor 530 and the server 550. Any format for communications may be used. In other embodiments, dedicated or direct communication is used.

The server 550 is a processor or group of processors. More than one server 550 may be provided. The server 550 is configured by hardware and/or software. The server 550 may include one or more image processors 530 configured to generate a visualization of a lung fissure. The one or more image processor 530 may operate serially or in parallel to process and render image data received from the imaging system 530.

The database 570 is a memory, such as a bank of memories, for storing data such as anonymized image volumes and two-dimensional images. The database 570 may be located locally or remotely.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for generating a visualization of a lung fissure, the method comprising:
    acquiring, by a medical image scanner, medical imaging data representing at least two adjacent lobes of a lung;
    generating, by an image processor, a mesh of a boundary between at least two adjacent lobes from the medical imaging data, the mesh comprising a plurality of mesh voxels;
    identifying, by the image processor, in the medical imaging data, fissure image data representing the lung fissure between the two adjacent lung lobes;
    augmenting, by the image processor, the mesh with the identified fissure image data;
    selecting, by the image processor, a projection point as a function of a type of the lung fissure;
    defining, by the image processor, a curved plane that is located behind the lung fissure from the projection point, wherein the curved plane includes a curvature selected as a function of a location of the projection point;
    projecting, by the image processor, the plurality of mesh voxels of the augmented mesh to the curved plane using a plurality of rays from the projection point to the curved plane;
    generating, by the image processor, a two-dimensional image of the projected augmented mesh comprising a single visualization of the entirety of the lung fissure; and
    providing, on a display, the two-dimensional image to a user.

2. The method of claim 1, wherein generating comprises:
    segmenting, by the image processor, each at least two adjacent lobes of the lung;
    identifying, by the image processor, a bronchial tree and vessel tree of the lung; and
    generating, a three-dimensional mesh of the lung from the segmentation and identification.

3. The method of claim 2, wherein generating the two-dimensional image further comprises:
    projecting, by the image processor, the bronchial tree and vessel tree onto the curved plane; and
    providing, by the image processor, the projected augmented mesh, the projected bronchial tree, and the projected vessel tree as the two-dimensional image to the user.

4. The method of claim 3, wherein the augmented mesh, the bronchial tree, and the vessel tree are rendered with different transparencies, different colors, or different transparencies and different colors.

5. The method of claim 1, wherein the medical imaging data is acquired from a computer tomography scan.

6. The method of claim 1, wherein identifying comprises:
identifying in the medical imaging data one or more pixels with higher attenuation values compared to surrounding tissues;
determining that the one or more pixels represent the lung fissure.

7. The method of claim 6, wherein augmenting comprises:
labeling a first mesh voxel for the plurality of mesh voxels as complete when the first mesh voxel matches up with a position of a fissure image voxel;
labeling a second mesh voxel as incomplete when the second mesh voxel does not match up with a position of a fissure image voxel; and
moving one or more voxels of the plurality of mesh voxels to correspond to a position of one or more fissure image voxels when the mesh is misaligned.

8. The method of claim 1, wherein the curvature is selected to limit a distortion at an edge of the lung fissure.

9. The method of claim 1, wherein the two-dimensional image is rendered with a different color for mesh voxels that represent incomplete fissure points than mesh voxels that correspond to identified fissure image data.

10. A method for generating a visualization of a lung fissure, the method comprising:
acquiring, by an image scanner, image data of a lung region;
identifying, by an image processor, lung data in the image data;
detecting, by the image processor, fissure data in the lung data;
defining, by the image processor, a point of view;
selecting, by the image processor, a projection point as a function of a type of the lung data;
defining, by the image processor, a curved plane that is located behind the lung data from the projection point, wherein the curved plane includes a curvature selected as a function of a location of the projection point;
projecting, by the image processor, the fissure data and the lung data onto the curved plane using a plurality of rays from the projection point to the curved plane; and
generating, by the image processor, from the point of view, a two-dimensional image of the projected fissure data and the projected lung data comprising a single visualization of the entirety of the lung fissure.

11. The method of claim 10, wherein generating further comprises:
rendering, by the image processor, in the curved plane, artery data.

12. The method of claim 10, wherein the medical imaging data is acquired from a computer tomography scan.

13. The method of claim 10 wherein detecting comprises:
identifying, by the image processor, one or more pixels in the imaging data with high attenuation values compared to surrounding tissues;
determining, by the image processor, that the one or more pixels represent the fissure data.

14. A system for generating a visualization of a lung fissure, the system comprising:
a medical scanner configured to acquire medical imaging data representing at least two adjacent lobes of a lung;
an image processor configured to generate a mesh of a boundary of at least two adjacent lobes from the medical imaging data and to identify in in the medical imaging data, fissure image data representing the lung fissure between the two adjacent lung lobes; the image processor further configured to augment the mesh with the identified fissure image data, select a projection point, define a curved plane with a curvature selected as a function of a location of the projection point, project the identified fissure image data to the curved plane using a plurality of rays from the projection point to the curved plane, and render a two dimensional image with the projected augmented mesh comprising a single visualization of the entirety of the lung fissure; and
a display configured to display the rendered two-dimensional image.

15. The system of claim 14, wherein the image processor is further configured to render the two-dimensional image with vessel data projected onto the curved plane.

16. The system of claim 14, wherein the image processor is further configured to render the two-dimensional image with a different color for mesh data that represents incomplete fissure points than mesh data that represents identified fissure image data.

* * * * *